United States Patent
Guzman

(10) Patent No.: US 8,899,859 B2
(45) Date of Patent: Dec. 2, 2014

(54) ANTISEPTIC APPLICATOR

(75) Inventor: Manuel Guzman, El Paso, TX (US)

(73) Assignee: Carefusion 2200, Inc., San Diego, CA (US)

( * ) Notice: Subject to any disclaimer, the term of this patent is extended or adjusted under 35 U.S.C. 154(b) by 0 days.

(21) Appl. No.: 13/328,454

(22) Filed: Dec. 16, 2011

(65) Prior Publication Data
US 2013/0156485 A1    Jun. 20, 2013

(51) Int. Cl.
*A61M 35/00* (2006.01)

(52) U.S. Cl.
USPC ............ 401/133; 401/108; 401/207; 401/264

(58) Field of Classification Search
USPC ......... 401/107, 108, 132, 203, 205, 207, 263, 401/264
See application file for complete search history.

(56) References Cited

U.S. PATENT DOCUMENTS

| | | | | |
|---|---|---|---|---|
| 3,091,374 A | * | 5/1963 | Schwartzman | 222/448 |
| 3,400,997 A | * | 9/1968 | Schwartzman | 401/186 |
| 3,519,364 A | * | 7/1970 | Truhan | 401/177 |
| 3,545,874 A | * | 12/1970 | Schwartzman | 401/186 |
| 3,653,779 A | * | 4/1972 | Schwartzman | 401/206 |
| 3,680,968 A | * | 8/1972 | Schwartzman et al. | 401/260 |
| 5,658,084 A | * | 8/1997 | Wirt | 401/132 |
| 6,932,532 B2 | * | 8/2005 | Schwartzman et al. | 401/264 |
| 7,325,993 B2 | * | 2/2008 | Gueret | 401/202 |
| 8,348,913 B2 | * | 1/2013 | Hoang et al. | 604/310 |
| 2008/0245314 A1 | * | 10/2008 | Brodowski et al. | 119/651 |
| 2010/0316430 A9 | * | 12/2010 | Cable et al. | 401/134 |
| 2012/0219346 A1 | * | 8/2012 | Law et al. | 401/132 |

* cited by examiner

*Primary Examiner* — David Walczak
*Assistant Examiner* — Joshua Wiljanen
(74) *Attorney, Agent, or Firm* — Arent Fox LLP

(57) ABSTRACT

An applicator assembly includes a head portion having a proximal, a distal end, and an interior portion defining a fluid chamber, a container slidably coupled to the body, a sealing member sealing an end of the container, and a lifting member, wherein the lifting member is mounted in the interior portion of the head portion and an interior of the container is placed in fluid communication with the application member by way of a fluid conduit that is formed around the sealing member from the container to the fluid chamber when the container is axially translated toward the head portion and the lifting member lifts the sealing member.

16 Claims, 2 Drawing Sheets

ANTISEPTIC APPLICATOR

BACKGROUND

1. Field

The present disclosure relates to an antiseptic applicator and method of use thereof, and more particularly, to a cap plug antiseptic applicator that requires the application of opposing forces to actuate release of a sealed solution, preferably an antimicrobial solution, from a self-contained reservoir toward a material arranged at a distal end of the applicator for receiving the solution.

2. Description of Related Art

Antiseptic applicators for the preparation of a patient prior to surgery, for example, are known and common in the prior art. Conventional applicators rely on various means of actuation to release a self-contained reservoir of antimicrobial solution for sterilization of the patient's skin. For example, a number of applicators are designed with a puncturing means. These applicators typically include a head with a spike, for example, and a sealed container or cartridge. A push or screw motion is employed to axially translate the head toward the sealed container so that the spike may pierce the sealed container and effectuate the release of the solution contained therein. Some examples of applicators using a puncturing means include U.S. Pat. Nos. 4,415,288; 4,498,796; 5,769,552; 6,488,665; and 7,201,525; and U.S. Pat. Pub. No. 2006/0039742.

Other conventional applicators rely on breaking an internally situated frangible container or ampoule through the application of a one-way directional force or a localized application of pressure. The directional force is typically applied longitudinally to one end of the ampoule by a pushing motion designed to force the ampoule to break under a compressive stress, sometimes at a predetermined area of stress concentration. Alternatively, a pressure may be applied to a localized section of the ampoule through a squeezing motion designed to crush a section of the frangible ampoule in order to release the antimicrobial solution contained therein. Some examples of applicators using frangible ampoules in the manner discussed above include U.S. Pat. Nos. 3,757,782; 5,288,159; 5,308,180; 5,435,660; 5,445,462; 5,658,084; 5,772,346; 5,791,801; 5,927,884; 6,371,675; and 6,916,133.

Conventional antiseptic applicators, as described above, often require special packaging and/or handling during shipping and prior to use. For example, with the puncture type applicators, preventive measures are required to prevent an inadvertent push against either end of the device that may result in the puncturing of the sealed container and the premature discharge of the solution. A user must often use both hands to effectively overcome the preventive measures and activate the applicator for use. In addition, conventional antiseptic applicators often rely on the exertion of pressure on the walls of an applicator, for example, to break a frangible ampoule or squeeze the solution from the container toward an application material. The use of frangible ampoules requires special care to avoid breaking as a result of inadvertent pressure or dropping during shipping or prior to use. Furthermore, the components of a conventional applicator, such as the broken ampoule or the puncture spike, often impede the free flow of the solution from the container. There exists a need in the field for a novel antiseptic applicator that avoids the complications associated with conventional applicators, especially an applicator that will allow for effective one hand actuation and application of a solution without impediments to the free flow of the solution from the container to the application material.

SUMMARY

In accordance with aspects of the present invention, an applicator assembly may include a head portion having a proximal end, a distal end, and an interior portion defining a fluid chamber; a container slidably coupled to the body; a sealing member sealing an end of the container; an application member attached to the distal end; and a lifting member mateable with the sealing member, wherein the lifting member is mounted in the interior portion of the head portion and an interior of the container is placed in fluid communication with the application member by way of a fluid conduit that is formed around the sealing member from the container to the fluid chamber when the container is axially translated toward the head portion and lifting member lifts the sealing member.

In accordance with another aspect of the present invention, the applicator assembly may further include a separable closing member sealing the other end of the container from the end having the breakable membrane.

In accordance with another aspect of the present invention, the applicator assembly may include an annular securing ring provided on an exterior of a sidewall of the container for mating with a first retention channel configured into an interior of the head portion to apply resistance to the axial movement of the container in relation to the head portion.

In accordance with yet another aspect of the present invention, the applicator assembly may include a second retention channel configured into the interior of the head portion and disposed closer toward the distal end than the first annular retention channel.

In accordance with another aspect of the present invention, a mechanical stop may be provided to secure the container in a predetermined position until the stop is released prior to actuation of the applicator.

It will become readily apparent to those skilled in the art from the following detailed description, wherein it is shown and described only exemplary configurations of an applicator assembly. As will be realized, the invention includes other and different aspects of an applicator and assembly and the various details presented throughout this disclosure are capable of modification in various other respects, all without departing from the spirit and scope of the invention. Accordingly, the drawings and the detailed description are to be regarded as illustrative in nature and not as restrictive.

DETAILED DESCRIPTION

Figure 1:
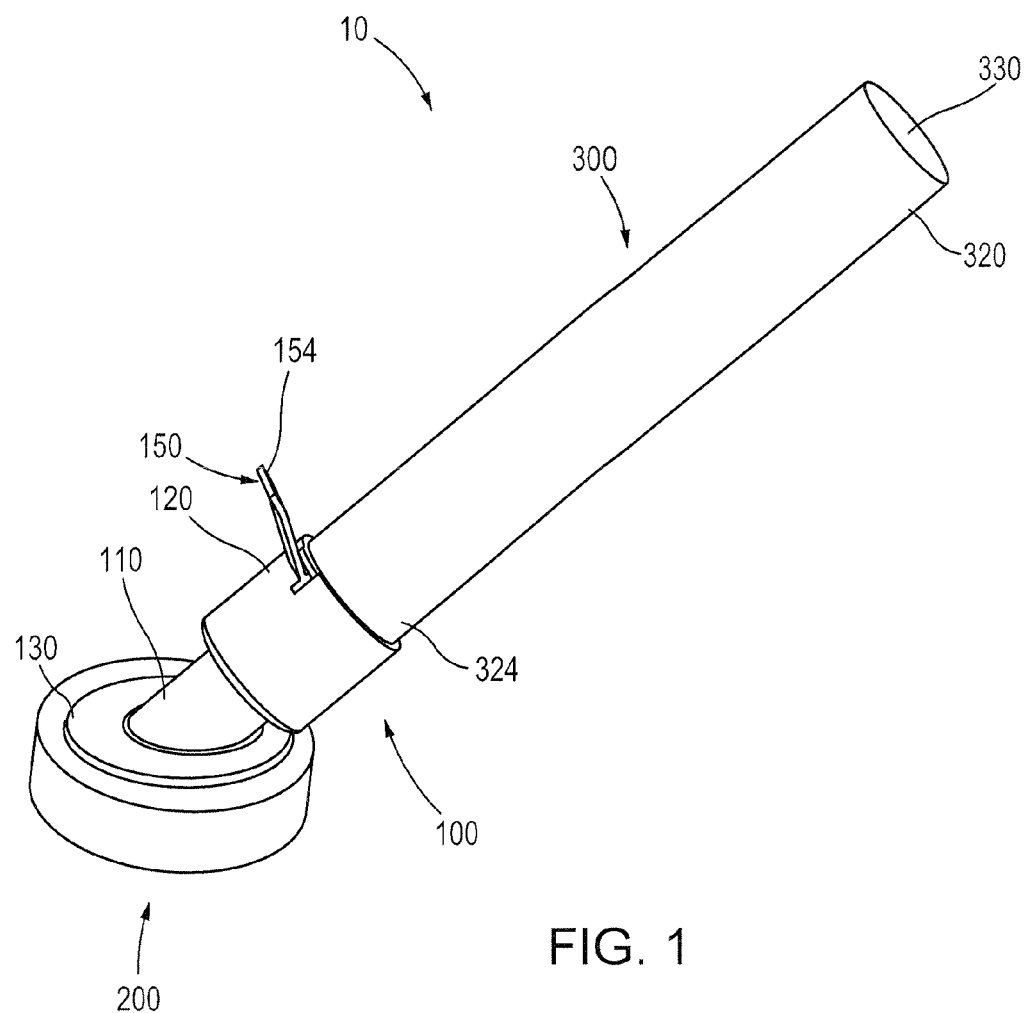
FIG. 1 is a perspective view of an antiseptic applicator, in accordance with certain aspects of the present invention.

Various aspects of an antiseptic applicator may be illustrated by describing components that are coupled, attached, and/or joined together. As used herein, the terms "coupled", "attached", and/or "joined" are used to indicate either a direct connection between two components or, where appropriate, an indirect connection to one another through intervening or intermediate components. In contrast, when a component is referred to as being "directly coupled", "directly attached", and/or "directly joined" to another component, there are no intervening elements present.

Relative terms such as "lower" or "bottom" and "upper" or "top" may be used herein to describe one element's relationship to another element illustrated in the drawings. It will be understood that relative terms are intended to encompass different orientations of an antiseptic applicator in addition to the orientation depicted in the drawings. By way of example, if an antiseptic applicator in the drawings is turned over, elements described as being on the "bottom" side of the other elements would then be oriented on the "top" side of the other elements. The term "bottom" can therefore encompass both an orientation of "bottom" and "top" depending on the particular orientation of the apparatus.

Various aspects of an antiseptic applicator may be illustrated with reference to one or more exemplary embodiments. As used herein, the term "exemplary" means "serving as an example, instance, or illustration," and should not necessarily be construed as preferred or advantageous over other embodiments of an antiseptic applicator disclosed herein.

Figure 2:
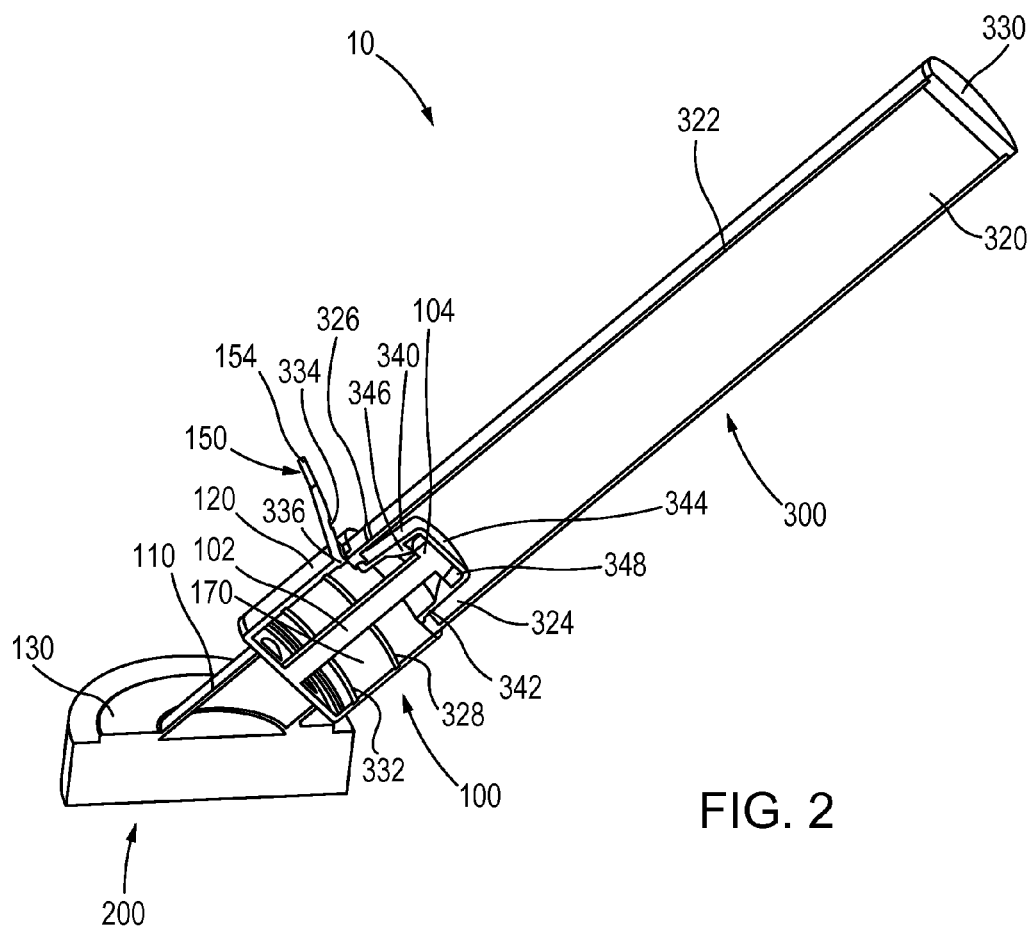
FIG. 2 is a side cutaway view of an antiseptic applicator, in accordance with certain aspects of the present invention.

The antiseptic applicator may be compact and ergonomically designed. As shown in FIGS. 1 and 2, an antiseptic applicator 10 may comprise a substantially hollow head portion 100, which may be cylindrical in shape, an application member 200 mounted to or proximate to a distal end 110 of the head portion 100, and a solution container 300 slidably received by a proximal end 120 of the head portion 100. The solution container 300 may be cylindrical in shape to position concentrically with the head portion 100. The solution container may be formed with a grasping mechanism, such as an area of crosshatching, for example, or a raised or recessed area integrated into a side wall 322 of the container 300, to enhance the ability of a user to hold and/or push the solution container 300 in one direction with one hand, in order to translate the solution container 300 in an axial direction toward the distal end 110 of the head portion 100.

The application member 200 may be formed from a foam sponge material, for example, or any suitable material that allows the controlled application of the contained solution from the solution container 300 to a surface external to the applicator 10. The material chosen may be porous with a particular soak rate, for example, or may be provided with structural features, including slits or apertures, to direct and control the flow rate of the solution through the application member 200. The head portion 100 may be configured to have a mounting flange 130 at or proximate to the distal end 110. The mounting flange 130 provides a surface for affixing the application member 200 to the head portion 100.

The solution container 300 is preferably a self-contained structure, formed of a suitable material, such as a polymer, preferably a high-density polyethylene plastic, that is flexible, yet resistant to deformation and chemical leaching. The container 300 may be filled with various liquids such as antiseptics or medicaments, chemical compositions, cleansing agents, cosmetics, or the like, and preferably an antimicrobial liquid or gel composition, such as a solution containing an alcohol, aldehyde, anilide, biguanide (i.e., chlorohexadine gluconate), octenidine dihydrochloride, diamidine, halogen-releasing agent, silver compound, peroxygen, and or phenols, for antiseptic application to a patient prior to surgery. The container 300 is designed to withstand various heat and chemical sterilization techniques, which may be performed sequentially with a solution filling process, in accordance with techniques that are well known in the art, such as a blow-fill-seal technique.

As shown in FIG. 2, the container 300 may be an elongated cylinder formed by the sidewall 322. A closing member 330 may be provided at the proximal end 320 and a sealing member 340 formed toward a distal end 324 of the container 300 to seal shut an interior of the container 300. The closing member 330 may be integrally formed with the container 300 or, for example, may be a separate component connected to the container, such as an end cap for mating via a threaded connection with the proximal end 320, or a plug that may be press fit or heat welded to the container 300, for sealing shut the open proximal end 320. In accordance with aspects of the present invention, the sealing member 340 may comprise a closure plug provided at or toward the distal end 324 of the container 300, and solution may be filled into the container 300 through either or both the open proximal end 320 of the container 300 prior to the container 300 being sealed shut with the closing member 330 and the open distal end 324 of the container 300 prior to application of the sealing member 340.

The sealing member 340 may be formed of a suitable material, such as a high-density polyethylene plastic, having enough strength to effectively seal the distal end 324 of the container 300 and prevent leaching of the contained solution. In an aspect of the present invention, the sealing member may comprise a plug. The sealing member may include a mating portion 342 and a receiving portion 344. The mating portion may be shaped to mate with the distal end 324 of the container 300. For example, the mating portion may be sized to create a friction fit with the distal end 324 of the container 300. By this design, the mating portion 342 of the sealing member 340 may be mated with the container 300 to provide a liquid tight seal. The receiving portion 344 is configured to allow a lifting member 102 to contact and preferably extend into sealing member 340. The receiving portion 344 may include a retaining member 346. The retaining member may be an element that is capable of preventing retraction of lifting member 102, once the lifting member 102 has been engaged with the receiving portion 344. For example, as shown in FIG. 2, the retaining member 346 may be a bias ramp that extends radially in a direction toward the center of the sealing member 340. The ramp may be resilient so that when a force is applied in a radial direction away from the center of sealing member, the ramp flexes, but then returns to the original position once the force is no longer applied. The ramp may also be positioned so that that a gap 348 is present between the remainder of the ramp and the end of the sealing member 340. The gap may be sized to allow a lip portion 104 of the projection member 102 to fit therein.

As shown in FIGS. 1 and 2, the sealed container 300 having a solution contained therein may be slidably inserted into the proximal end 120 of the head portion 100. A holding member, such as an annular securing ring 326, may be provided on the exterior of the side wall 322 toward the insertion end 324 of the container 300. The holding member may cooperate with a corresponding member on the head portion 100, such as a first retention channel 328 configured into an interior of the head portion 100 to limit the axial movement of the container 300 in relation to the head portion 100 and to prevent the separation of the container 300 from the head portion 100 once joined in a final assembled position. In accordance with yet other aspects of the present invention, the holding member may be provided on the head portion 100 and cooperate with a corresponding member on the container 300 to prevent the separation of the container 300 from the head portion 100.

In accordance with yet another aspect of the present invention, a mechanical stop 150 may be provided to secure the container 300 in the assembled position until the stop 150 is intentionally released prior to activation of the applicator 10. In this manner, the lifting member 102 may be prevented from displacing the sealing member 340 during handling, storage and transport of the applicator 10. The mechanical stop 150 may be attached to or integral to the proximal end 120 of the head portion 100. In accordance with another aspect of the present invention, the mechanical stop may alternatively be provided on a portion of the container 300. A holding mechanism (not shown), such as a snap fit channel 334, for example, may be provided on an inner side of the mechanical stop 150 to engage the holding member when the mechanical stop 150 is pressed against the container 300, or against the head portion 100 in an alternative configuration, to be maintained in a storage position. With the holding mechanism thus engaged, the container 300 may be prevented from axial movement toward and away from the head portion 100 during assembly, handling or transport of the applicator 10. To disengage the mechanical stop 150, a user simply applies pressure against a release tab 154 to maneuver the mechanical stop 150 away from the container 300, or head portion 100 in an alternative configuration, and disengage the holding mechanism. The release tab 154 may be angled to provide clearance between the stop 150 and the container 300 when the stop 150 is hinged in a closed position with the holding mechanism engaged. A user may thus easily disengage the stop 150 with one hand by applying pressure with one finger, such as a thumb or index finger, against the release tab 154 while holding the applicator 10.

In accordance with other aspects of the present invention, the mechanical stop 150 may be formed with a detent 336 on an interior surface to further prevent axial movement of the container 300 toward the head portion 100. The detent 336 may extend into the interior portion of the head portion 100 near where the stop 150 is hinged and engage the distal end 324 of the container 300 when in a closed position. Upon the rotational release of the stop 150 by pressure exerted against the release tab 154, the detent 336 rotates along with the stop 150 and releases the distal end 324 of the container to slide into the head portion 100. The stop 150 may be configured to lock into an open position once actuated.

As shown in FIG. 2, with the container 300 concentrically mounted in the head portion 100, as described above, and the application member 200 mounted to close off the distal end 110 of the head portion 100, the fluid chamber 170 may be formed in the distal end of the head portion 100 between the application member 200 and the sealing member 340. A fluid metering device, such as a pledget, for example, may be optionally provided in the fluid chamber 170 to further control and/or direct the flow of solution from the container 300 when the assembly 10 is in use.

To activate the applicator 10 and release the solution from the container 300, a user may grasp the container 300 with one hand. The mechanical stop 150 may be disengaged by using a finger on the same hand to exert pressure against the release tab 154 and disengage the holding mechanism. The user may either use their other hand to hold the head portion 100 and/or may press the head portion 100 against a stable surface while applying force against the container 300 to slide the container into the head portion 100. The application of the compressive force dislodges the securing ring from the first annular retention channel, if present, allowing the container 300 to translate from a proximally disposed position further into the head portion 100. Continued applied force on the container 300 axially translates the container 300 toward the distal end of the head portion 100.

As shown in FIG. 2, one end of the lifting member 102 may be formed with a lip portion 104 and another end of the lifting member may be integral with the distal end 110 of the head portion 100. Furthermore, support struts (not shown) may be provided to secure the lifting member 102 at a predetermined position in the head portion 100 of the applicator 10. As the container 300 translates toward the distal end 110 of the head portion 100, the lifting member 102 displaces the sealing member 340. For example, if the sealing member is secured to the container via a friction fit, the sealing member will lift once the force applied on the sealing member is sufficient to overcome the friction force. With the sealing member 340 displaced, via the positioning of the applicator 10 with the application member 200 situated below the container 300, the solution drains from the container 300 into the fluid chamber 170 under its own weight. Further axial translation of the container 300 in a distal direction relative to the head portion 100 may accelerate and increase the lifting of the sealing member 340, which may increase the flow of the solution from the container 300 into the fluid chamber 170. Additionally, the lifting member 102 may be secured within the sealing member 340 such that translation of the container 300 in an axial direction away from the head 200 will re-seal the container 300 or reduce the size of the flow path of the solution. That is, the sealing member 340 preferably is shaped so that translation of the container 300 in a direction toward the head 200 may cause the sealing member to lift, while translation of the container 300 in a direction away from the head 200 may cause the sealing member to retract. Thus, an operator can reduce or increase the amount of solution that flows into the head 200.

As shown in FIG. 2, in an example aspect of the present invention, as the container 300 is translated towards the head 200, the lip portion 104 slides over a bias ramp 346 of plug sealing member 340. Because the ramp 346 is flexible, as the lip portion 104 passes across the ramp 346, the ramp is flexed radially toward a side wall of the plug sealing member 340. Once the lip portion 104 passes beyond the ramp 346 and settles into the gap 348, the ramp 346 biases back to the original position, away from the side wall of the plug sealing member. With the ramp 346 back in the bias position the lip portion 104 can only contact the flat side of the ramp and is unable to further flex the ramp. Thus, when the container 300 is translated in a direction away from the head 200, the lip portion 104 will apply a force on the flat side of the ramp, which will in turn pull the plug sealing member 340 back toward the initial sealed position.

The solution may soak into, or otherwise flow through, the application material 200 at a specified volume and rate. The fluid chamber 170 may serve to accumulate and distribute the solution evenly over substantially the entire area of the application material 200. Once the application material 200 is engorged, for example, the solution may then be applied to a patient by wiping the distal surface of the application material 200 against the skin.

According to another aspect of the present invention, a second corresponding member, such as a second retention channel 332 may be provided along the interior of the head portion 100 that is disposed closer toward the distal end 110 than the first corresponding member. The holding member on the container 300 may thus engage the second retention channel after a predetermined distance of translation into the head portion 100 to substantially secure the container 300 and maintain the applicator 10 in an open position.

The previous description is provided to enable any person skilled in the art to practice the various embodiments described herein. Various modifications to these embodiments will be readily apparent to those skilled in the art, and the generic principles defined herein may be applied to other embodiments. For example, rather than the container 300 being concentrically mounted in the head portion 100, the head portion 100 may slidably mount into the container 300. Thus, the claims are not intended to be limited to the embodiments shown herein, but is to be accorded the full scope consistent with the language claims, wherein reference to an element in the singular is not intended to mean "one and only one" unless specifically so stated, but rather "one or more." All structural and functional equivalents to the elements of the various embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for."

What is claimed is:

1. An applicator assembly comprising:
   a head portion having a proximal end, a distal end, and an interior portion defining a fluid chamber;
   a container slidably coupled to the head portion;
   a sealing member sealing an end of the container;
   an application member attached to the distal end;
   a lifting member mateable with the sealing member, wherein the lifting member is mounted in the interior portion of the head portion and an interior of the container is placed in fluid communication with the application member by way of the fluid chamber when the container is axially translated within the head portion and the lifting member lifts the sealing member; and
   a closing member sealing the other end of the container from the end having the sealing member.

2. The applicator assembly of claim 1, wherein the closing member is separable from the container.

3. The applicator assembly of claim 2, wherein the closing member is connected to the container via a threaded connection.

4. The applicator assembly of claim 1, wherein the sealing member comprises a hollow body portion mateable with the lifting member.

5. The applicator assembly of claim 4, wherein the lifting member comprises a lip portion and the sealing member comprises a retaining member mateable with the lip portion.

6. The applicator assembly of claim 5, wherein the retaining member is a flexible ramp.

7. The applicator assembly of claim 4, wherein the lifting member lifts the sealing member when the container translates toward the distal end of the head portion.

8. The applicator assembly of claim 4, wherein the lifting member retracts the sealing member when the container translates away from the distal end of the head portion.

9. The applicator assembly of claim 1, wherein the interior of the container is placed in fluid communication with the application member by way of the fluid chamber when the container is axially translated toward the application member.

10. An applicator assembly comprising:
    a head portion having a proximal end, a distal end, and an interior portion defining a fluid chamber;
    a container slidably coupled to the head portion;
    a sealing member sealing an end of the container;
    an application member attached to the distal end;
    a lifting member mateable with the sealing member, wherein the lifting member is mounted in the interior portion of the head portion and an interior of the container is placed in fluid communication with the application member by way of the fluid chamber when the container is axially translated within the head portion and the lifting member lifts the sealing member; and
    an annular securing ring provided on an exterior of a sidewall of the container for mating with a first retention channel configured into an interior of the head portion to apply resistance to the axial movement of the container in relation to the head portion.

11. The applicator assembly of claim 10, further comprising a second retention channel configured into the interior of the head portion and disposed closer toward the distal end than the first retention channel.

12. An applicator assembly comprising:
    a head portion having a proximal end, a distal end, and an interior portion defining a fluid chamber;
    a container slidably coupled to the head portion;
    a sealing member sealing an end of the container;
    an application member attached to the distal end;
    a lifting member mateable with the sealing member, wherein the lifting member is mounted in the interior portion of the head portion and an interior of the container is placed in fluid communication with the application member by way of the fluid chamber when the container is axially translated within the head portion and the lifting member lifts the sealing member; and
    a mechanical stop to secure the container in a predetermined position until the stop is released prior to actuation of the applicator.

13. The applicator assembly of claim 12, wherein the mechanical stop comprises a hinged portion of the proximal portion of the head portion.

14. The applicator assembly of claim 13, wherein the mechanical stop further comprises a securing mechanism to prevent axial translation of the container.

15. The applicator assembly of claim 14, wherein the securing mechanism comprises a snap fit channel for engaging a holding member on an exterior of the container to secure the applicator assembly in a storage position when the mechanical stop is pressed against the container.

16. The applicator assembly of claim 14, wherein the securing mechanism comprises a detent that engages an insertion end of the container.

* * * * *